US00PP15309P3

(12) United States Plant Patent
Köhne

(10) Patent No.: US PP15,309 P2
(45) Date of Patent: Nov. 9, 2004

(54) AVOCADO TREE NAMED 'MERENSKY 2'

(50) Latin Name: *Persea americana*
Varietal Denomination: Merensky 2

(76) Inventor: Josef Stefan Köhne, Westfelia Estate, P.O. Box 14, Duivelskloof (ZA), 0835

( * ) Notice: Subject to any disclaimer, the term of this patent is extended or adjusted under 35 U.S.C. 154(b) by 0 days.

(21) Appl. No.: 10/046,490

(22) Filed: Oct. 25, 2001

(65) Prior Publication Data

US 2003/0051278 P1 Mar. 13, 2003

Related U.S. Application Data

(60) Provisional application No. 60/317,871, filed on Sep. 7, 2001.

(51) Int. Cl.[7] ..... A01H 5/00
(52) U.S. Cl. ..... Plt./200
(58) Field of Search ..... Plt./200

(56) References Cited

U.S. PATENT DOCUMENTS

PP12,439 P2 * 3/2002 Krome et al. ..... Plt./200

OTHER PUBLICATIONS

UPOV ROM GTITM Computer Database, GTI JOUVE Retrieval Software 2002/05, citation(s) for Latas, Merensky, 'Merensky 2', and 'Dusa'.*

Anon. Avocado Important Commercial cultivars Cultivar: Edranol ARC—Institute for Tropical and Subtropical Crops Http:/www.arc.agric.za/institutes/itsc/main/avocado/edranol.htm.*

List of publications http://www.kypros.org/ARI/hopubl1.html pg. 2.*

AvoResearch vol. 1, Issue May 2, 2001 California Avocado Commission.*

Westfalia Nursery: Avocado & Mango Young Trees for Export; Reasearch and Development http://www.westfalia-nursery.co/za/resdev.htm.*

Ettinger http://www.ucavo.ucr.edu/AvocadoWebSite% . . . vocadoVarieties/VarietyLisa/Ettinger.html.*

Edranol http://www.ucavo.ucr.edu/AvocadoWebSite% . . . vocadoVarieties/VarietyLisa/Edranol.html.*

Fuerte http://www.ucavo.ucr.edu/AvocadoWebSite% . . . vocadoVarieties/VarietyLisa/Fuerte.html.*

Menge, J.A. Screening and Evaluation of New Rootstocks with Resistance to *Phytophthora cinnamomi* http://www.avocado.org/static/growerres/symposium/19mengeroot.php.*

* cited by examiner

*Primary Examiner*—Kent Bell
*Assistant Examiner*—W C Haas
(74) *Attorney, Agent, or Firm*—Aaron T. Borrowman; Kelly Lowry & Kelly, LLP

(57) ABSTRACT

A new and distinct variety of avocado tree having many characteristics similar to those of 'Duke 7' that is characterized by strong resistance to *Phytophthora cinnamoni,* and which bears more fruits than the 'Duke 7' variety when 'Hass' is grafted thereon.

10 Drawing Sheets

Botanical classification: *Persea americana* Mill.

BACKGROUND OF THE INVENTION

The present invention generally relates to avocado trees. More particularly, the present invention relates to a new and distinct variety of avocado tree, *Persea americana,* with significantly improved resistance to root rot.

A tree or seedling rootstock was discovered in an avocado orchard heavily infested with root rot, caused by *Phytophthora cinnamoni* at Westfalia Estate, South Africa. Most trees in that orchard died of root rot, however, the tree of the present invention was one of the few survivors and looked very healthy.

In the Westfalia nursery, an asexual reproduction of the tree rootstock was made by taking a bud bearing stick from a rootstock shoot and grafting onto a nurse seedling in the nursery. The grafted wood was subsequently rooted following standard procedures for producing clonal avocado trees. The trees were grafted with the scion 'Hass' in the nursery and planted in field trials in which the tree always showed the same superior resistance to root rot as the original seedling. The clones or propagules of the tree have been found to be identical to the original seedling in all distinguishing characteristics.

A Simple Sequence Repeat (SSR) DNA fingerprinting technique was performed on avocado leaves of various varieties, including the 'Merensky 2'. Three samples from the same cultivar were used. Aside from leaves of the 'Merensky 2', three other rootstock selections from the Westfalia nursery, 'Edranol', 'Ettinger', 'Fuerte', and 'Duke 7' were used. Total genomic DNA was isolated from the leaf samples using 2% CTAB and chloroform:isoamylalcohol (24:1). The SSR primers were: A1E11, A4F08, A7G04, of which the A7G04 primer was found not useful and the A1E11 primer most useful in clearly distinguishing the cultivars, except two of the rootstocks from the Westfalia nursery. No variation could be found between the different samples from the same cultivar. It was concluded that two of the cultivars from the Westfalia nursery were identical. However, there were differences found between the 'Merensky 2' and the other varieties, and very clear differences found between the 'Merensky 2' and the 'Duke 7' variety.

In California, the 'Merensky 2' avocado trees have been planted and grown at the "University of California South Coast Field Station", in Irvine, Calif.

SUMMARY OF THE INVENTION

The invention relates to a new and distinct variety of an avocado tree having many characteristics similar to that of 'Duke 7'. The invention is characterized by superior resistance to root rot, such as that caused by *Phytophthora cinnamoni*, as compared to 'Duke 7'. The fruit of the present invention has been found to be slightly larger than that of 'Duke 7', and also has a better taste than that of 'Duke 7'.

An additional report characteristic of 'Merensky 2' is its affect on the bearing of the 'Hass' avocado. 'Hass' grafted onto the instant cultivar bears more fruits than 'Hass' grown on 'Duke 7'.

BRIEF DESCRIPTION OF THE DRAWINGS

The accompanying photographs show the tree and fruit of the present invention. In such photographs.

BOTANICAL DESCRIPTION OF THE PLANT

Figure 1:
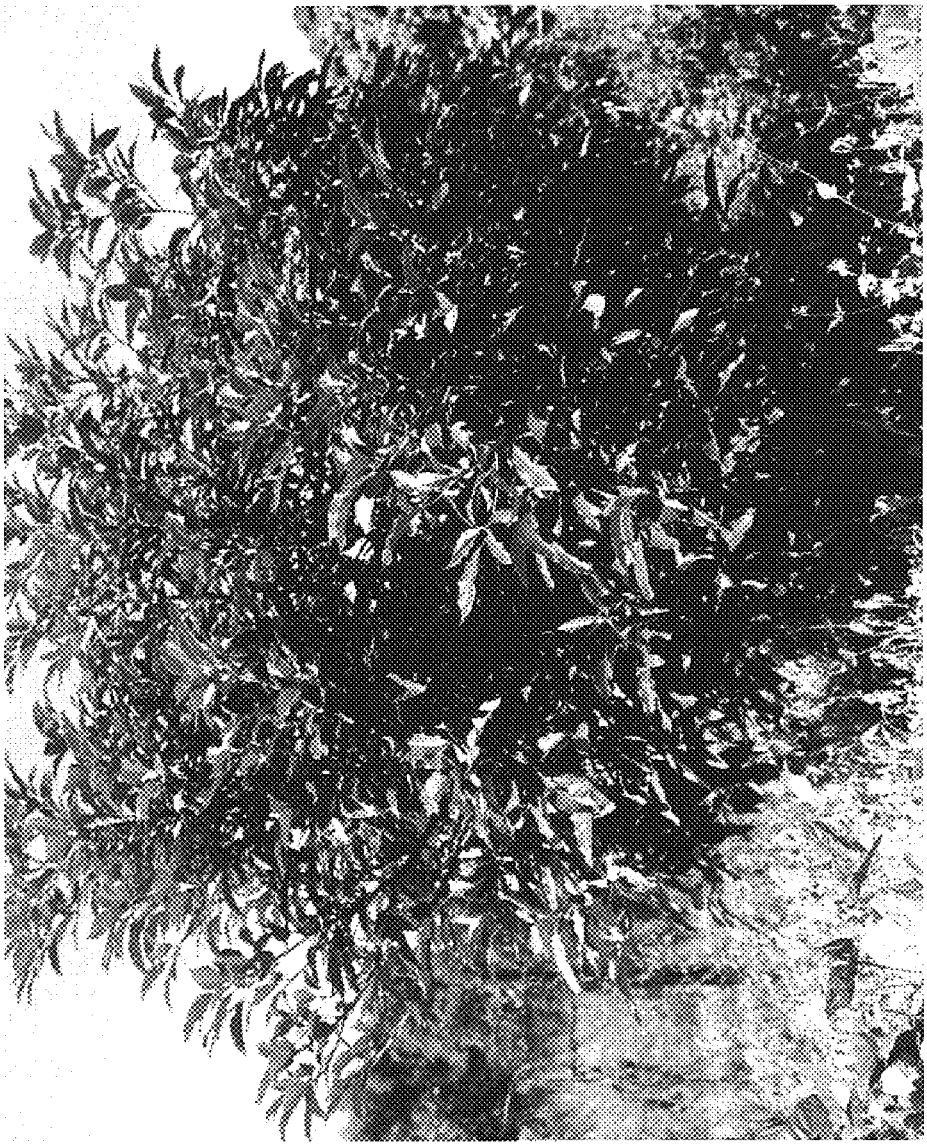
FIG. 1 shows a 'Merensky 2' variety in South Africa.
Figure 2:
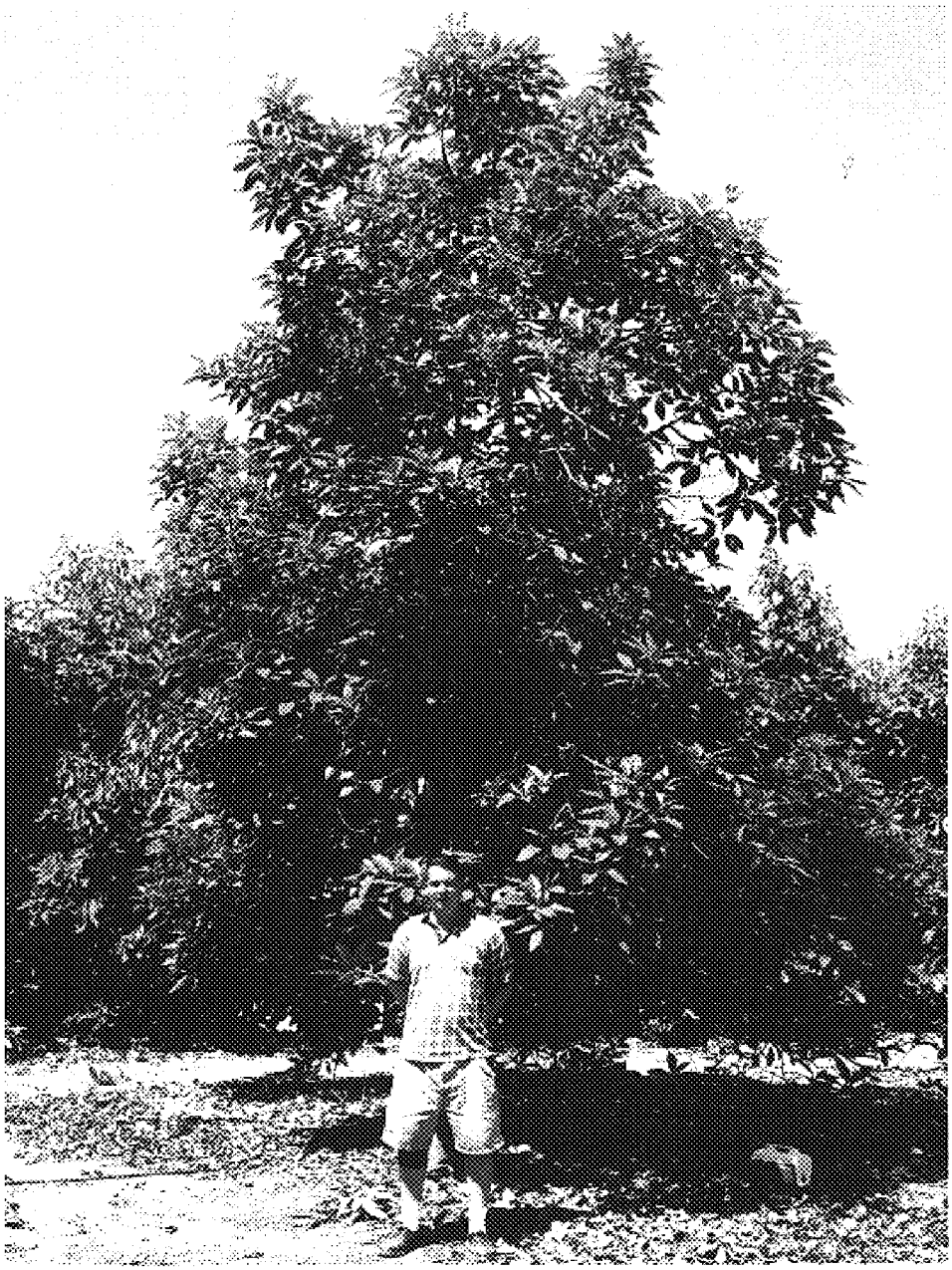
FIG. 2 shows a mature 'Merensky 2' in California.
Figure 3:
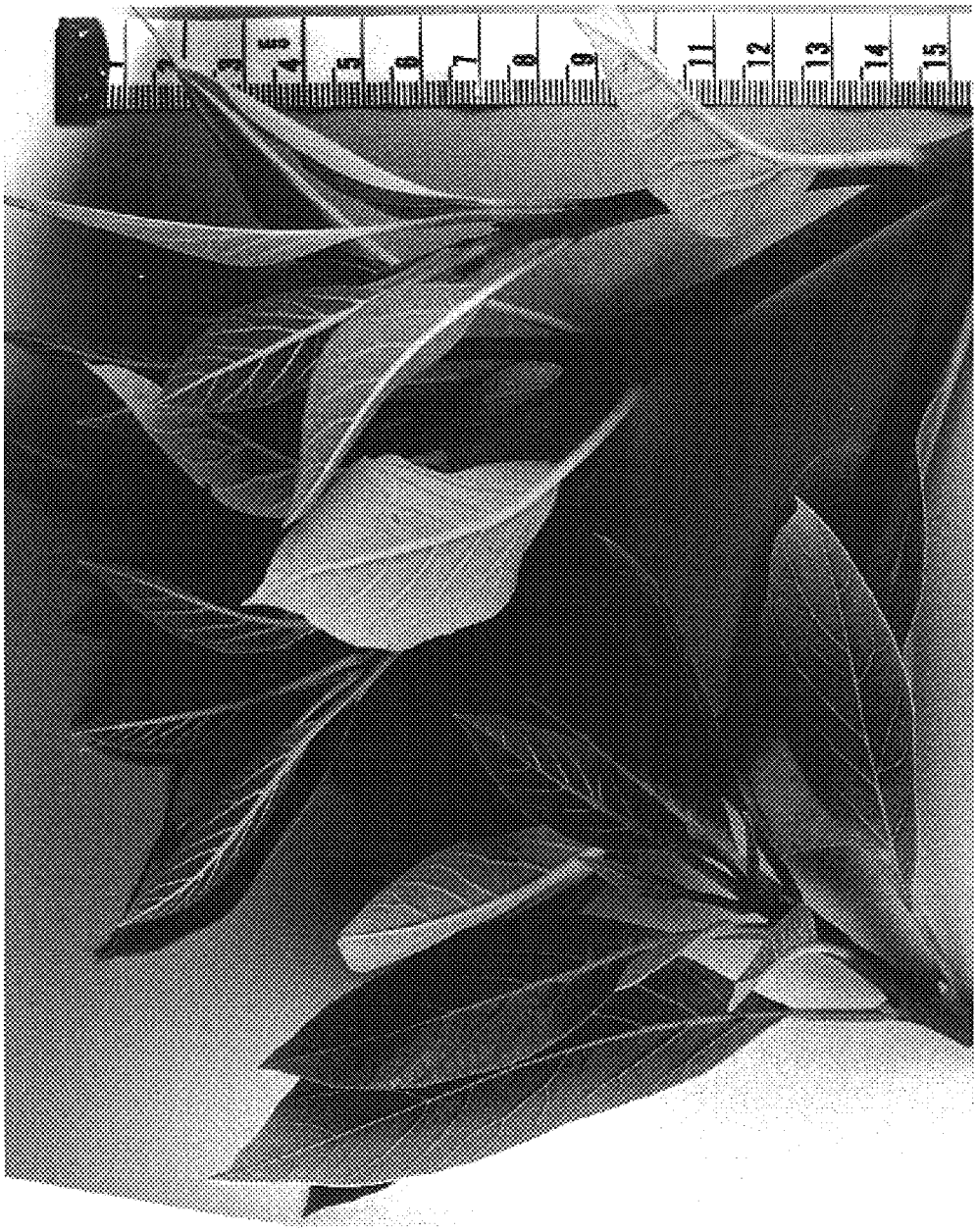
FIG. 3 shows flush from a 'Merensky 2'.
Figure 4:
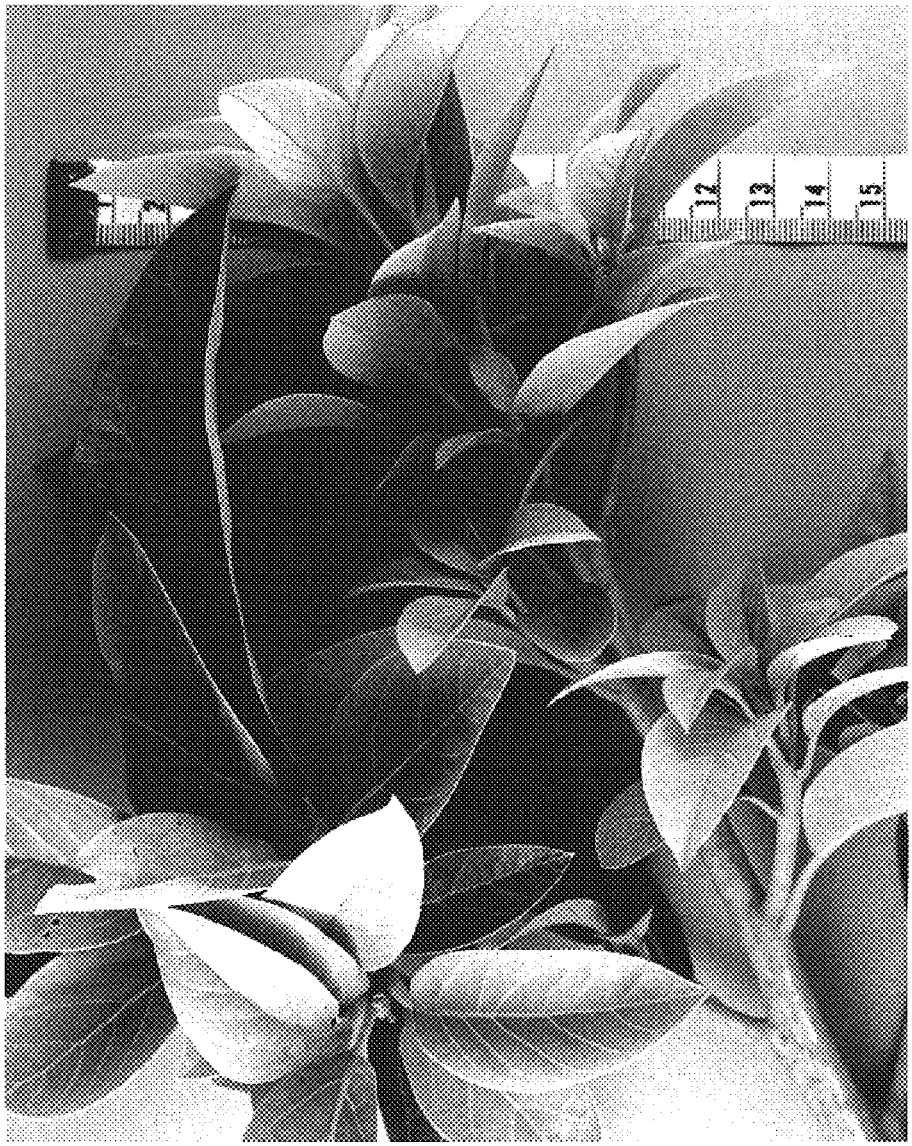
FIG. 4 shows flush from 'Duke 7'.
Figure 5:
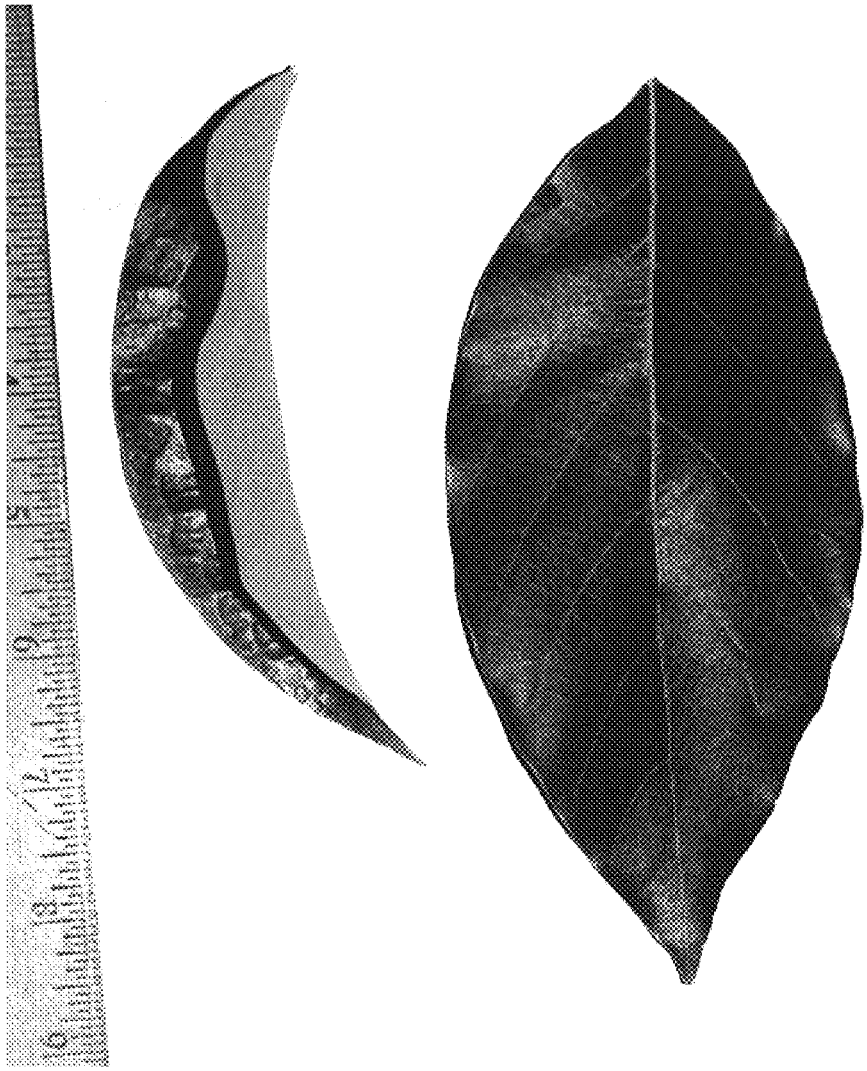
FIG. 5 shows a comparison of mature leaves of the 'Duke 7' (left) and 'Merensky 2' (right)
Figure 6:
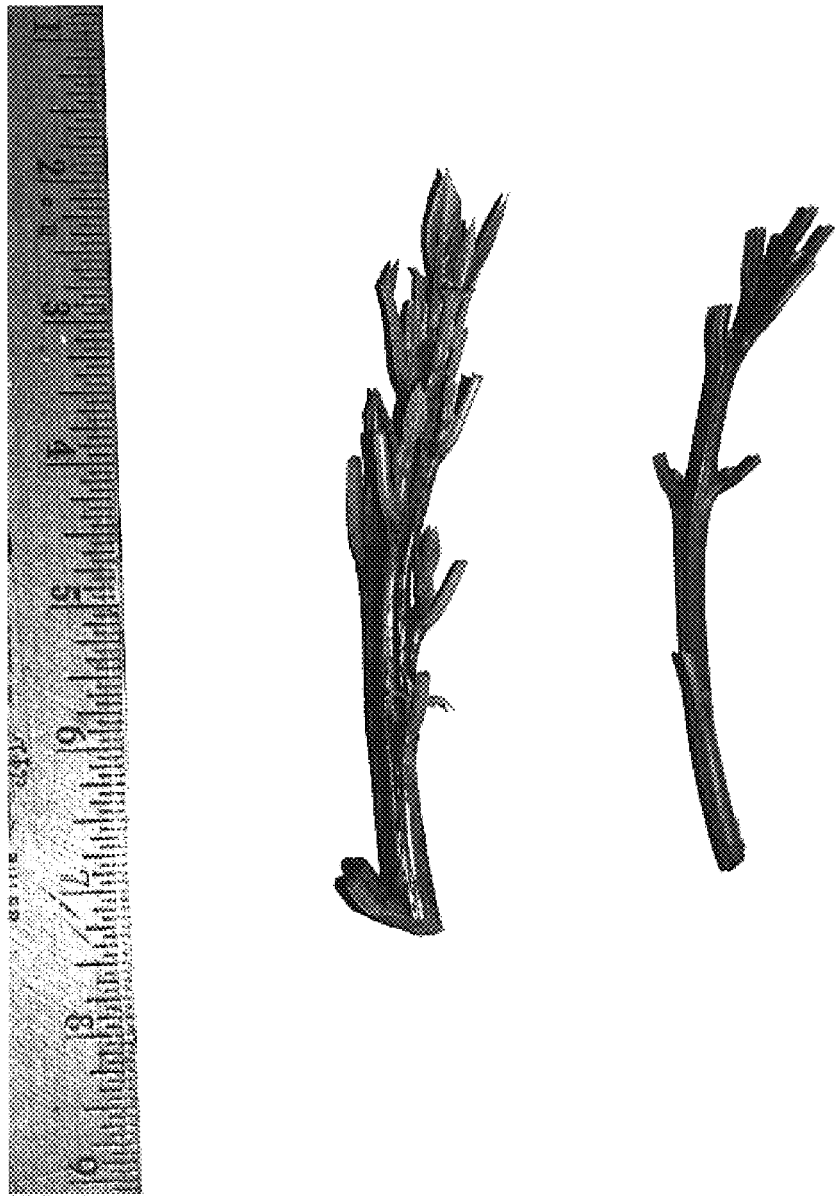
FIG. 6 shows a comparison of succulent stems of 'Duke 7' (left) and 'Merensky 2' (right)

In those instances where precise color assessment can be made, references are to The Royal Horticultural Society (R.H.S.) Colour Chart. In other instances, generally, color terms are used in accordance with an ordinary dictionary significance. The instant cultivar 'Merensky 2' is described as a plant as a whole in the following description, with the exception as an rootstock for a specific scion when reference is made to root rot resistance and yields. The following description is taken from a four year old cultivar located at Groenkloof Block 2, Westfalia Estate, South Africa.

Cultivar name: 'Merensky 2'.
Botanical name: *Persea americana.*
Form: Tree.
Cultural conditions: Westfalia Estate, Groenkloof section, is situated in north-eastern South Africa (latitude 23.45 S, longitude 30.05 E, altitude 750 m above sea level). The soil type is a fine-loamy, mixed paleuduit (USDA), 1975. Soil Taxonomy, Soil Conservation Service, Agriculture Handbook No. 436, Washington) with a clay content of 40%. Soil analysis prior to planting indicated a need for phosphate and pH adjustment. Superphosphate was applied to address the phosphate needs and the low soil pH (5.6) was amended to pH 6.5 by applying dolomitic lime. Nutrition requirements were based on annual leaf analyses and fertilizers spread under the tree by hand. There is a deficiency of the trace elements zinc and boron which are supplemented annually. Soil erosion is prevented by planting an annual legume cover crop. Soil moisture is monitored by means of tensionmeters and irrigation is applied by micro-sprinklers aimed to wet 100% of soil in the drip zone. Climatic data: Long term average monthly maximum (MAXT)/minimum (MINT) temperature and monthly rainfall for Westfalia Estate, Groenkloof section.

| | JAN | FEB | MAR | APR | MAY | JUN | JULY |
|---|---|---|---|---|---|---|---|
| MAX T(° C.) | 27.8 | 28.1 | 127.2 | 25.7 | 23.9 | 21.6 | 22.3 |
| MINT (° C.) | 17.2 | 17.7 | 16.7 | 13.9 | 9.8 | 5.7 | 5.8 |
| RAIN (mm) | 149.3 | 245.4 | 153.8 | 107.1 | 28.5 | 30.9 | 5.0 |

| | AUG | SEP | OCT | NOV | DEC | YEAR |
|---|---|---|---|---|---|---|
| MAX T(° C.) | 23.4 | 24.3 | 25.4 | 28.5 | 28.9 | 25.3 |
| MINT (° C.) | 7.6 | 10.8 | 13.0 | 14.7 | 16.7 | 12.5 |
| RAIN (mm) | 21.8 | 62.9 | 107.5 | 106.5 | 161.3 | 1180 |

Tree size: Four year old ungrafted 'Merensky 2': height 2.0 meters, width 1.8 meters.
Growth habit: Medium vigor, medium size, with a spreading growth habit, whereas the 'Duke 7' is more upright. The vigor of the 'Merensky 2' alone has not been scrutinized, however the vigor of 'Hass' scion is grafted onto the instant cultivar as determined by trunk circumference measurements in years two through four after planting in an orchard with high *Phytophthora cinnamoni* pressure is 18.1 cm in year two, 23.6 cm in year three, and 27.6 cm in year four.
Wood: One-year old branch: Normally green, smooth bark, having inconspicuous lenticels.
Main stem:
*Bark.*—New wood green (RHS 147B), old wood greyish brown (RHS 199B) and (N199B), having a corky texture.
*Young shoot(flush).*—The intensity of anthocyanin coloration is medium, as compared to the absent or very weak coloration in 'Duke 7'. The color of the flush is reddish (RHS 176A), whereas the 'Duke 7' is a light yellow-green (RHS 144B).
*Lenticels.*—The plant has medium conspicuousness of lenticels, whereas the 'Duke 7' variety is strong. The color of the lenticels in both the present variety and the 'Duke 7' is purplish (RHS 187C). The lenticels are 1 mm long, and have a concentration of 30 lenticels per square cm.
Foliage:
*Type.*—Single leaf.
*Young leaf.*—The present variety has an orange-brown (RHS 172A) color on its upper side, whereas the 'Duke 7' variety has a light orange-green (RHS 199A). The glossiness of the young leaf on flush in medium in the present variety. The lower surface color and texture for the underside of new foliage is a grey-orange color (RHS 174A), dull leaves gradually expand and mature to a green color as the growth flush terminates.
*Mature leaf.*—The present variety has a length of approximately 17 centimeters and a width of approximately 7 centimeters, where the 'Duke 7' variety has a length of approximately 11.5 centimeters and a width of approximately 5.0 centimeters. Thus, the ratio of length to width in the present variety is 2.4, whereas in the 'Duke 7' variety it is 2.3. The shape of the leaves of both the present variety and 'Duke 7' variety is lanceolate to elliptic. The upper side of a mature leaf in the present variety and of the 'Duke 7' variety is of a medium gloss, having a dark green (RHS 147A) color. The color of the lower side of a mature leaf in the present variety is medium green (RHS 147B), whereas in the 'Duke 7' variety it is blue green (RHS N138B). Both the present variety and the 'Duke 7' variety have prominent veins on the lower side of the mature leaf. The mature leaf of the present variety is generally flat in cross section, whereas the 'Duke 7' is folded upwards. Whereas reflexing of the apex of a mature leaf is present in the 'Duke 7' variety, it is absent in the present variety. The colors of the petiole of the mature leaf is generally the same as the 'Duke 7' variety, that is yellow-green (RHS 145A). Similar to the 'Duke 7' variety, the mature leaf of the present variety has an anise aroma. Old foliage is medium green (RHS N138C) with dull finish and fully expanded. Veins are prominent and in relief, yellow-green in color (RHS N144A).

Fruit:

*Quality.*—Very good quality, whereas the 'Duke 7' variety can be watery.

*Form.*—The shape of the fruit of the present is obovoid, whereas the fruit of the 'Duke 7' variety is obovate.

*Size.*—The present variety of fruit has a length of approximately 11 centimeters, and a width of approximately 7 centimeters for a length to width ratio of 1.6. By comparison, the size of the mature fruit of the 'Duke 7' variety is 8.9 centimeters in length by 5.5 centimeters in width, or the same ratio of length to width as the present variety.

*Skin color.*—When ripe, the fruit of the present invention has a very dark green (RHS 137A) skin color.

*Skin texture.*—The texture of the skin is similar to that of 'Duke 7' variety, and very smooth.

*Longitudinal ridges.*—Whereas longitudinal ridges are absent in the 'Duke 7' variety, one strong and long longitudinal ridge is present in the present variety.

*Skin.*—The skin of the present variety is very thin and membranous, and the adherence of the skin to the flesh of the fruit is very strong. In the 'Duke 7' variety, the skin is thin, but the adherence of the skin to the flesh of the fruit is weak.

*Color.*—The main color of the flesh of the fruit of the present variety is light yellow (RHS 154D) and, with the color of the flesh next to the skin being yellow-green (RHS 144A). The width of the more intensely colored area of the flesh next to the skin is approximately 3 millimeters. Fibers in the flesh are conspicuous.

*Seed.*—The seed of the present variety is approximately 4.8 centimeters in length and approximately 4.2 centimeters in width. By contrast, the seed of the 'Duke 7' variety is approximately 4.4 centimeters in length and approximately 3.4 centimeters in width. The seed shape (in longitudinal section) of both the present variety and the 'Duke 7' variety is ovate. The color of a fresh seed coat of the present variety is orange-brown (RHS 165A).

Bloom: Similar to the 'Duke 7' variety, the present variety begins to flower and bloom in August, in South Africa. The flowering time in California has not been carefully studied. Bloom period in California of the instant cultivar, as with other avocado varieties, varies according to latitude and temperatures. However, a 'Merensky 2' located in Irvine, Calif. has been found to bloom between November $10^{th}$ through February 25th.

Harvest: In South Africa, the present variety is harvested in March, whereas the 'Duke 7' is harvested in February. Although not carefully studied in California, it is believed that the fruit will be harvested sometime in November to as late as May. Fruit is not used from the present variety. Instead, the variety is used to produce cuttings and thus propagated as a rootstock, due to its resistance to *Phytophthora cinnamoni*. Shoots of the present variety are grafted with another fruit bearing variety above the area where the rooting occurs.

Figure 7:
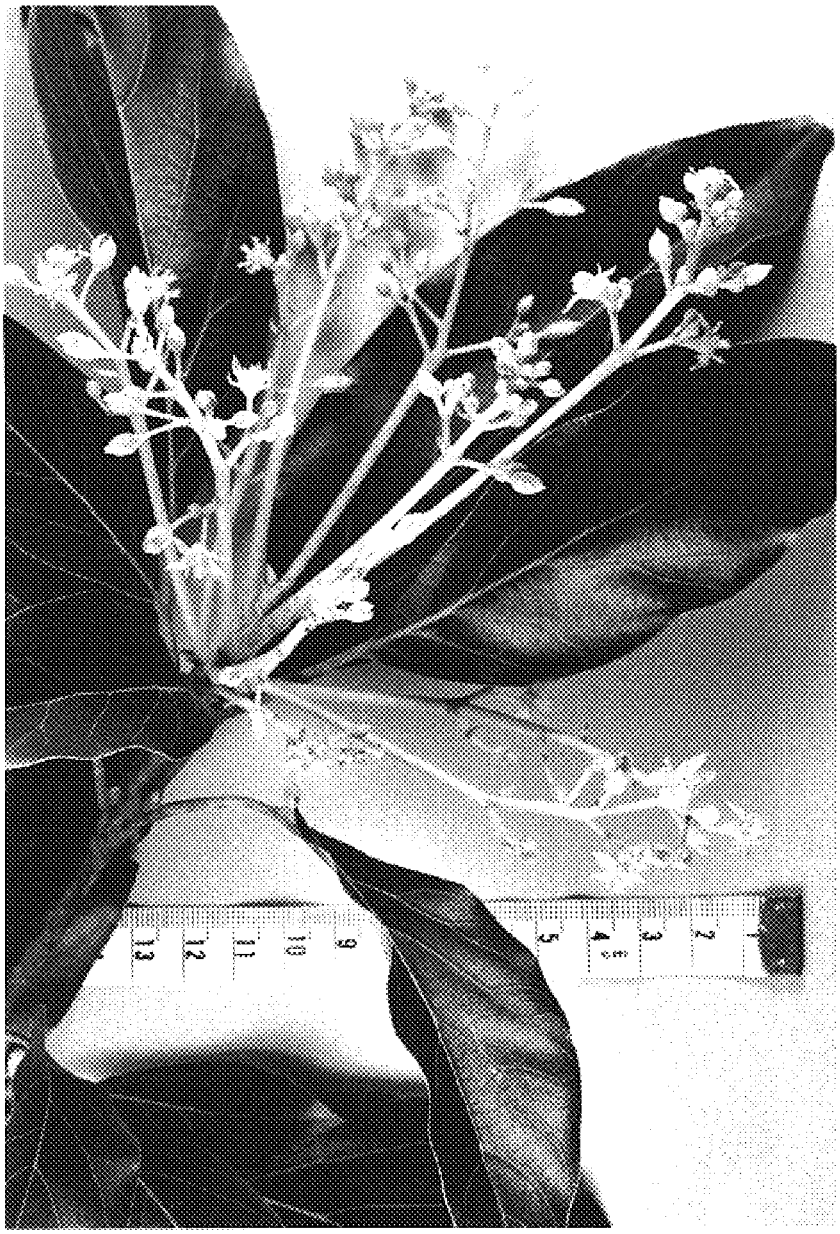
FIG. 7 shows the 'Merensky 2' in bloom.
Figure 8:
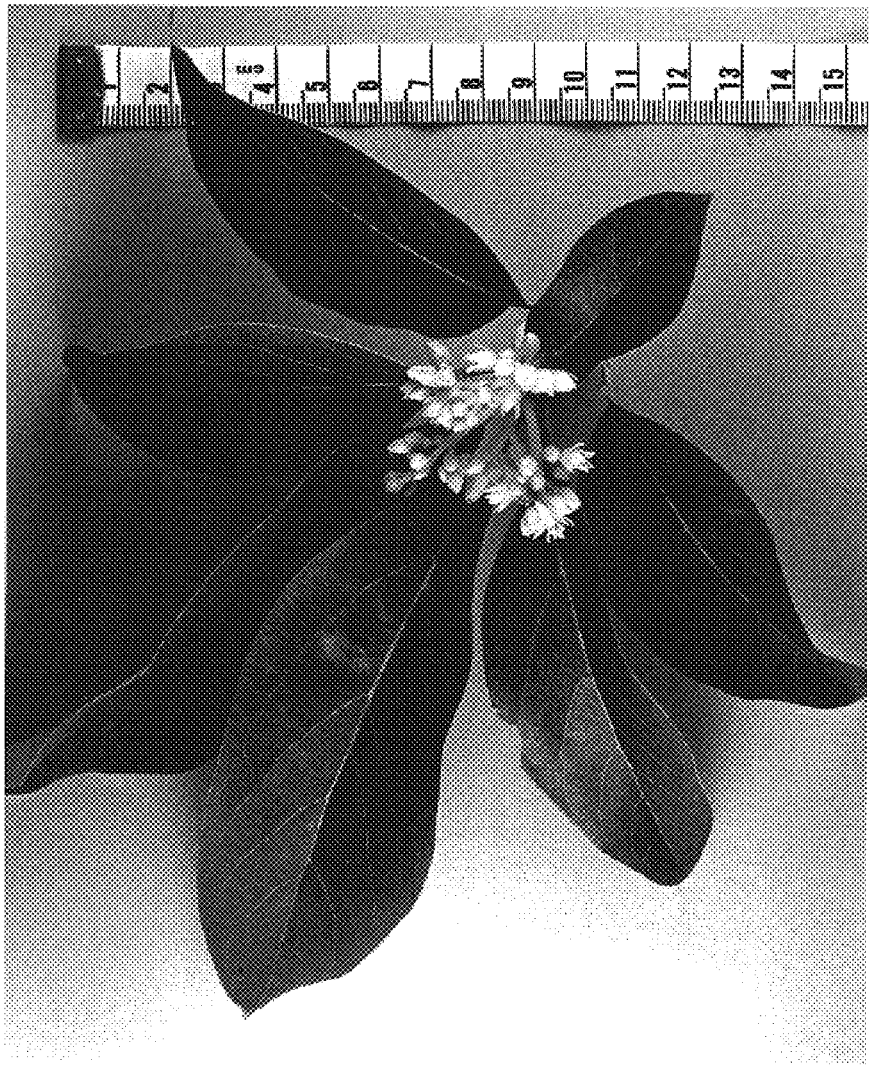
FIG. 8 shows the 'Duke 7' variety in bloom.
Figure 9:
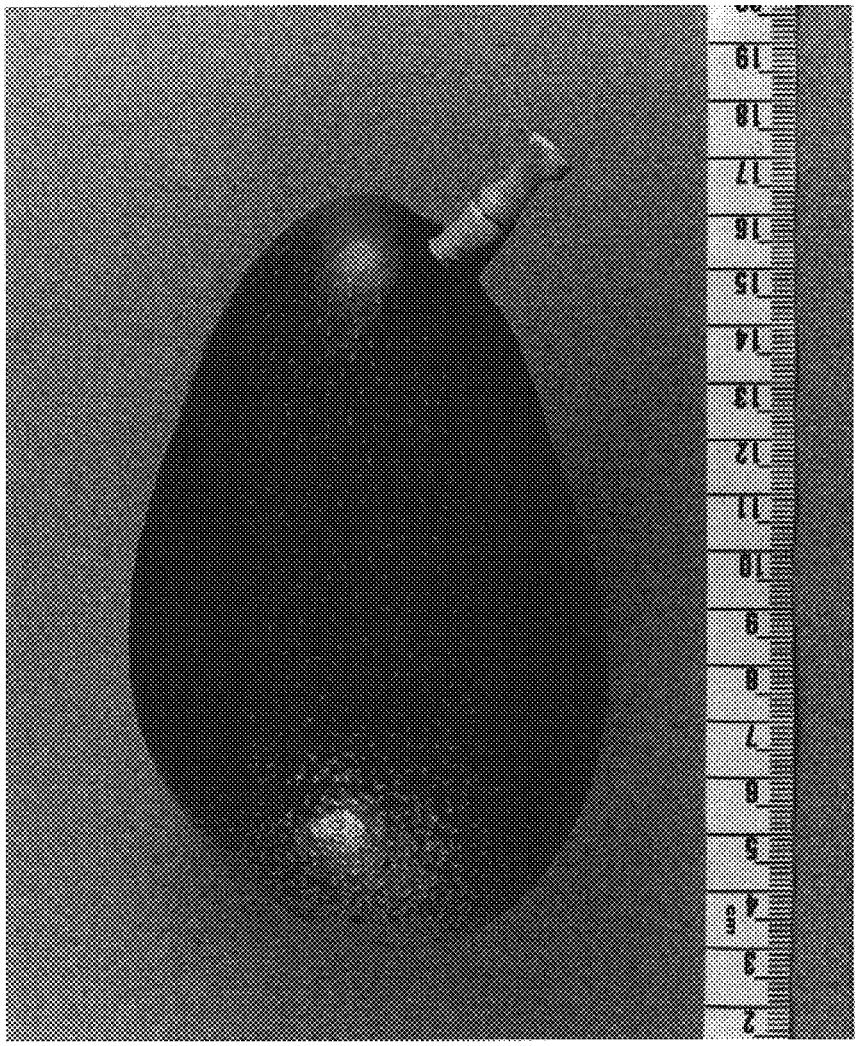
FIG. 9 shows an exterior view of a mature fruit of the 'Merensky 2' variety.
Figure 10:
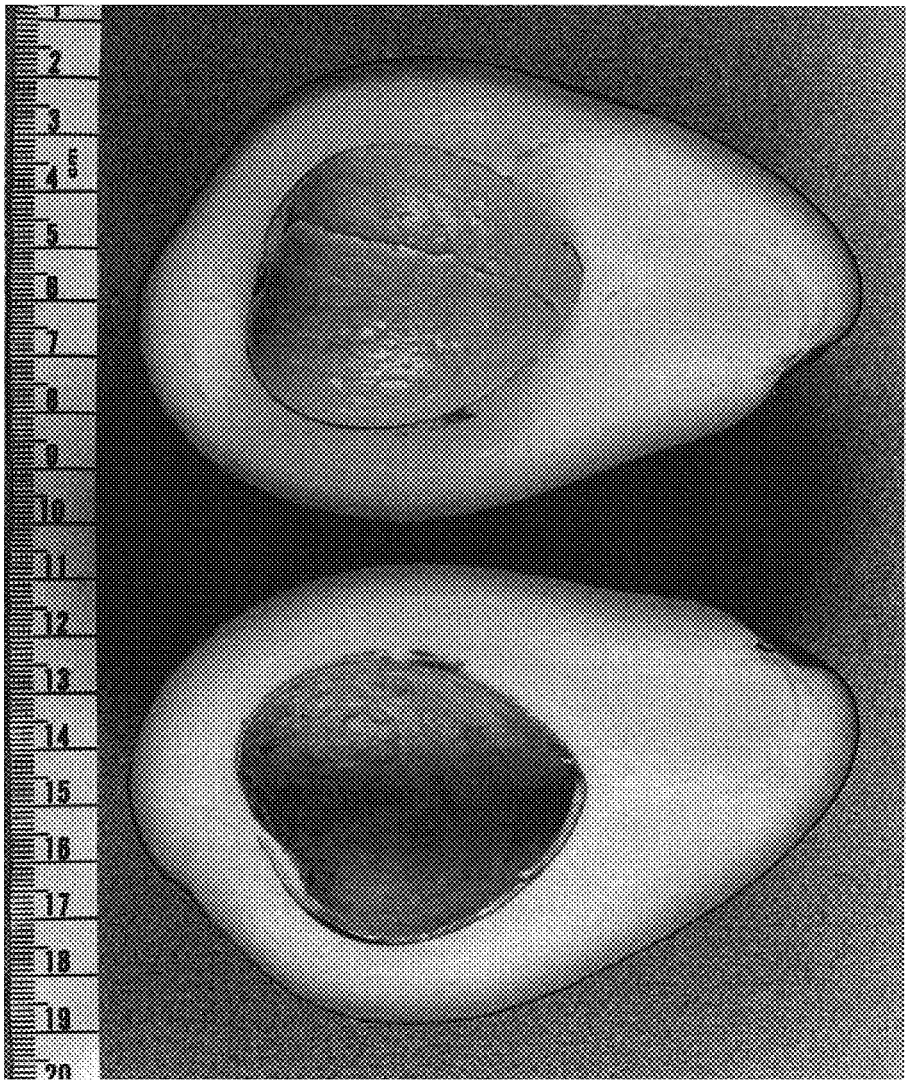
FIG. 10 shows views of the fruit flesh and stone of the 'Merensky 2'.

Flower: The present cultivar belongs to Group B (female opening occurs in the afternoon and male opening the next morning). The instant cultivar inflorescence is similar to that of the 'Hass' variety regarding size, shape, color, anthers, pistils, petals and number, as shown in FIG. 7. The flowers of the plant do not have a distinct fragrance.

*Type.*—Synchronous dichogamy, and borne in panicles.

*Bud size.*—Approximately 6 mm in length and approximately 4 mm in diameter.

*Bud shape.*—Ovoid.

*Bud color.*—Commonly near yellow green group RHS 149D.

*Opening.*—The present cultivar belongs to Group 'B': female opening (i.e. with a mature pistil) occurs in the afternoon, the flower closes over night, and male opening (i.e. with mature stamens) occurs the next morning; the flower's opening cycle lasts 20–24 hours. The 'B' flower type is the compliment of 'A' ('Hass'). Commonly avocados of the 'B'-type are used for enhancing pollination of 'Hass'.

*Petals.*—Borne in two whorls or three perianth lobes. The petals possess entire margins and petal coloration is near yellow green RHS 145D.

*Stamen.*—There commonly are nine fertile stamens with each having two basal orange nectar glands, and three stamisoda. The anthers are tetrathecal.

*Pistil.*—The single pistil with a slender style and small stigmatic surface has one carpel with one ovule. The ovary is superior.

*Pedicel.*—Commonly approximately 7 mm in length and approximately 1.8 mm in diameter. The coloration is near yellow green RHS 145C.

*Number of flowers.*—There are approximately 110 to 170 flowers per inflorescence.

*Full bloom.*—Bloom period at Westfalia Estate Groenkloof section varies with temperatures. However, a 'Merensky 2' located at the Groenkloof section has been found to bloom from July $3^{rd}$ through September $25^{th}$.

*Fragrance.*—The flowers of the plant are not fragrant.

Disease: Whereas the 'Duke 7' variety has medium resistance to *Phytophthora cinnamoni,* the present variety is significantly more resistant to *Phytophthora cinnamoni* than the 'Duke 7' variety.

The tree and its fruit herein described may vary in 'Merensky2', as herein described and illustrated.

What is claimed is:

1. An avocado tree as shown and described, characterized by superior resistance to root rot, and bearing more fruit when 'Hass' is grafted thereon than 'Hass' grown on 'Duke 7'.

* * * * *